US010660188B2

(12) United States Patent
Denner et al.

(10) Patent No.: US 10,660,188 B2
(45) Date of Patent: May 19, 2020

(54) ELECTROSTATIC DISCHARGING DEVICE

(71) Applicant: Schunk Wien Gesellschaft m.b.H, Vienna (AT)

(72) Inventors: Gerhard Denner, Vienna (AT); Thomas Radinger, Weinzierl (AT)

(73) Assignee: SCHUNK WIEN GESELLSCHAFT M.B.H., Vienna (AT)

( * ) Notice: Subject to any disclaimer, the term of this patent is extended or adjusted under 35 U.S.C. 154(b) by 402 days.

(21) Appl. No.: 15/521,826

(22) PCT Filed: Oct. 19, 2015

(86) PCT No.: PCT/EP2015/074182
§ 371 (c)(1),
(2) Date: Apr. 25, 2017

(87) PCT Pub. No.: WO2016/066469
PCT Pub. Date: May 6, 2016

(65) Prior Publication Data
US 2017/0251544 A1    Aug. 31, 2017

(30) Foreign Application Priority Data

Oct. 31, 2014    (DE) .................. 10 2014 222 265

(51) Int. Cl.
*H05F 3/02*        (2006.01)
*B64D 45/02*      (2006.01)
(Continued)

(52) U.S. Cl.
CPC .............. *H05F 3/02* (2013.01); *B64D 45/02* (2013.01); *H05F 3/00* (2013.01); *A61N 1/14* (2013.01);
(Continued)

(58) Field of Classification Search
USPC ........................................ 361/212, 218, 220
See application file for complete search history.

(56) References Cited

U.S. PATENT DOCUMENTS 2,821,664 A    1/1958   Weaver et al.
7,193,836 B2   3/2007   Oh et al.
(Continued)

FOREIGN PATENT DOCUMENTS

CN         1702495 A      11/2005
CN       201033524 Y       3/2008
(Continued)

OTHER PUBLICATIONS

PCT English Language Translation of the International Preliminary Report on Patentability, PCT/EP2015/074182, dated May 11, 2017.
(Continued)

*Primary Examiner* — Danny Nguyen
(74) *Attorney, Agent, or Firm* — Quarles & Brady LLP

(57) ABSTRACT

A discharging device for discharging electrostatic charges from a shaft includes a conductor arrangement having at least two bending elastic conductors arranged on a holder and made of a carbon-fiber arrangement. The holder has two holder legs arranged on a common pivot axis, each holder leg serving to accommodate a terminal section of a conductor. The holder legs are pivotable relative to each other to enable a holder angle ($\alpha$) formed between the holder legs to be adjusted. The holder legs are lockable in a defined pivoted position.

14 Claims, 3 Drawing Sheets

(51) Int. Cl.
*H05F 3/00* (2006.01)
*B60R 16/06* (2006.01)
*H02G 13/00* (2006.01)
*A61N 1/14* (2006.01)

(52) U.S. Cl.
CPC ...... *B60R 16/06* (2013.01); *B65H 2301/5133* (2013.01); *H02G 13/40* (2013.01); *Y10S 57/901* (2013.01)

(56) References Cited

U.S. PATENT DOCUMENTS

2004/0233592 A1* 11/2004 Oh ................... G11B 19/2009
  361/23
2006/0228923 A1   10/2006 Swift et al.
2015/0239661 A1*  8/2015 Morris, III ............ B65D 90/46
  361/215

FOREIGN PATENT DOCUMENTS

| | | |
|---|---|---|
| CN | 203289729 U | 11/2013 |
| DE | 1909066 U | 1/1965 |
| DE | 7010427 U | 11/1970 |
| DE | 217668 A1 | 1/1985 |
| DE | 2002013001243 U1 | 3/2013 |
| EP | 1432085 A1 | 6/2004 |
| JP | H07319348 A | 12/1995 |

OTHER PUBLICATIONS

The Patent Office of the People's Republic of China, First Office Action and Search Report, Application No. 201580059628.1, dated May 28, 2018, 7 pages [English Language Translation Only].

PCT International Search Report, PCT/EP2015/074182, dated Dec. 16, 2015.

* cited by examiner

ELECTROSTATIC DISCHARGING DEVICE

CROSS-REFERENCE TO RELATED APPLICATIONS

This application represents the national stage entry of PCT International Application No. PCT/EP2015/074182 filed on Oct. 19, 2015 and claims priority to German Patent Application No. 10 2014 222 265.6 filed on Oct. 31, 2014. The contents of this application are hereby incorporated by reference as if set forth in their entirety herein.

BACKGROUND

The invention relates to a discharging device for discharging electrostatic charges from a shaft, comprising a conductor arrangement having at least two bending-elastic conductors arranged on a holder and made of a carbon fiber arrangement and running transverse to a shaft longitudinal axis, the conductors being connectable to a grounding conductor via their terminal sections, which are accommodated in the holder, and each having a shaft contact section, the shaft contact sections forming a contact arrangement for making contact with two circumferential contact areas of a shaft circumference, the contact areas being arranged opposite each other in a shaft contact plane W, in such a manner that the shaft contact sections are arranged tangentially to the shaft circumference when they are in contact with the shaft circumference, the holder having two holder legs arranged on a common pivot axis, each holder leg serving to accommodate a terminal section of a conductor and the holder legs being pivotable against each other in order for a holder angle α formed between the holder legs to be adjusted and the holder legs being lockable in a defined pivoted position.

From U.S. Pat. No. 7,193,836, a discharging device for discharging electrostatic charges from a shaft is known, in which a carbon-fiber arrangement made of a plurality of filaments is arranged on a holder which has an annular shape and is arranged coaxially to the shaft. For a physical contact with the shaft to be formed, shaft contact sections of the individual filaments are aligned normally to the shaft circumference. A physical contact between the filaments and the shaft circumference thus occurs merely at the axial ends of the filaments. Since the carbon fiber arrangement is arranged on the annular holder, the known discharging device is suitable only for a shaft with a defined circumference.

SUMMARY

The object of the present invention is to provide a discharging device that allows forming secure contact with a shaft circumference irrespective of the direction of rotation and that is suitable, moreover, for discharging electrostatic charges from shafts with different shaft diameters.

To attain this object, the discharging device according to the invention has the features of claim 1.

According to the invention, the discharging device is provided with a bending-elastic conductor arrangement which has at least two conductors arranged on a holder and made of a carbon fiber arrangement and running transverse to a shaft longitudinal axis of a shaft to be made contact with. The conductors can be connected to a grounding conductor via terminal sections accommodated in the holder. Each conductor has a shaft contact section, the shaft contact sections forming a contact arrangement for coming into contact with two circumferential contact areas of a shaft circumference, the circumferential contact areas being arranged opposite each other in a shaft contact plane. The shaft contact sections are arranged tangentially to the shaft circumference.

According to the invention, the holder has two holder legs which are arranged on a common pivot axis and can be pivoted against each other and each of which serves to accommodate a terminal section of a conductor and which can be pivoted relative to each other in order for a holder angle α formed between the holder legs to be adjusted and can be locked in a defined pivoted position.

Irrespective of whether the conductors of the conductor arrangement are connected to each other in one piece, i.e. whether the conductors each form a section of the conductor arrangement or whether they are each realized independently as separate conductors, adjusting a holder angle allows adjusting a contact distance defined between the shaft contact sections destined to come into tangential contact with the shaft circumference. In particular in case of a straight shape of the conductors, the contact distance between the shaft contact sections of the conductors is determined by the holder angle and by the distance between the pivot axis of the holder and the shaft longitudinal axis. This leads to multiple options of adjustment to special installation conditions for installation of the discharging device.

Similarly, owing to the bending-flexible design of the conductors, the contact force with which the shaft contact sections of the conductors come into tangential contact with the shaft circumference can be predetermined by suitably adjusting the holder angle and the holder distance defined by the distance between the pivot axis and the shaft longitudinal axis. Thus, a separate contact force device, such as a spring or the like, which acts between the holder legs, is superfluous.

In a preferred embodiment, the conductors of the conductor arrangement are realized as two independently realized conductor strands which are connected to each other in an electrically conductive manner via their terminal sections.

The electrically conductive connection between the terminal sections can take place via the grounding conductor in particular if the holder legs are not electrically conductive, i.e. if they are made of plastic or ceramic, for example.

If the electrically conductive connection between the terminal sections is formed via the holder legs, the conductors can be electrically connected to each other even if they are realized independently of each other without having to provide a component that would need to be provided specifically for this purpose. In this case, the grounding conductor can in particular be connected to one of the two holder legs without forming a direct connection to the conductors in order to achieve the desired discharging effect.

It is especially advantageous for the electrically conductive design of the holder legs if the holder legs are made of an electrically conductive material, the holder legs preferably being made of a carbon material.

Besides its good electrical conductivity, the use of graphite is especially suitable for forming the holder legs because graphite has particularly favorable tribological properties which ensure that an adjustment of the holder angle by relative rotation of the holder legs remains possible even after the discharging device has been used in a corrosive atmosphere.

The pivot axis is preferably formed by a bolt connecting the holder legs with each other and formed independently of the holder legs, allowing the holder legs to be designed identically and the holder legs preferably each having an eyelet with which they are arranged on the bolt.

In a preferred embodiment, if the holder legs are made of an electrically conductive material and the bolt is made of an electrically nonconductive material, the bolt can be used both to realize the pivot axis and to arrange the holder in an isolated manner relative to the surroundings of the holder, i.e. an installation location of the holder.

It is particularly preferred for the holder legs to have a mold cavity for receiving a conductive filling material embedding the terminal sections in order to accommodate the terminal sections because accommodation by embedding in the filling material allows achieving both a secure mechanical connection and a secure electrical contact between the conductors and the holder legs.

Preferably, a locking means for locking the holder legs relative to each other is realized between the holder legs, the locking means preferably having meshing locking elements formed integrally with the holder legs, to making it unnecessary to separately provide a component enabling the locking of the holder legs. In this way, in particular the number of components or parts needed for realizing the discharging device is kept low.

It is particularly advantageous if the carbon fiber arrangement of the conductors has a fiber network which is provided with a coating made of pyrolytically deposited carbon, the coating of pyrocarbon thus not only serving to densify a contact surface of the conductor but additionally also forming an envelope supporting the fiber network, the envelope providing the desired bending-elastic properties of the conductor in cooperating with the fiber network, the conductor having a bending flexibility that can also be influenced in particular by the thickness of the coating.

Producing the coating by application of the CVI (chemical vapor infiltration) method has proven particularly advantageous because this method does not only yield the desired surface coating but additionally also leads to the formation of bonding forces between the individual filaments of the fiber network.

It proves particularly advantageous if the fiber network is realized as an envelope of a unidirectional fiber strand running in the longitudinal direction of the conductors and having filaments that run substantially parallel to each other, the gaps between the fibers thus forming capillaries that allow the use of capillary effects for transporting fat or humidity away from the shaft circumference.

For increasing the bending stiffness of the conductor, it is advantageous if the fiber network is provided with a resin matrix.

Hereinafter, an advantageous embodiment of the invention will be explained in more detail with the aid of the drawing.

DETAILED DESCRIPTION

Figure 1:
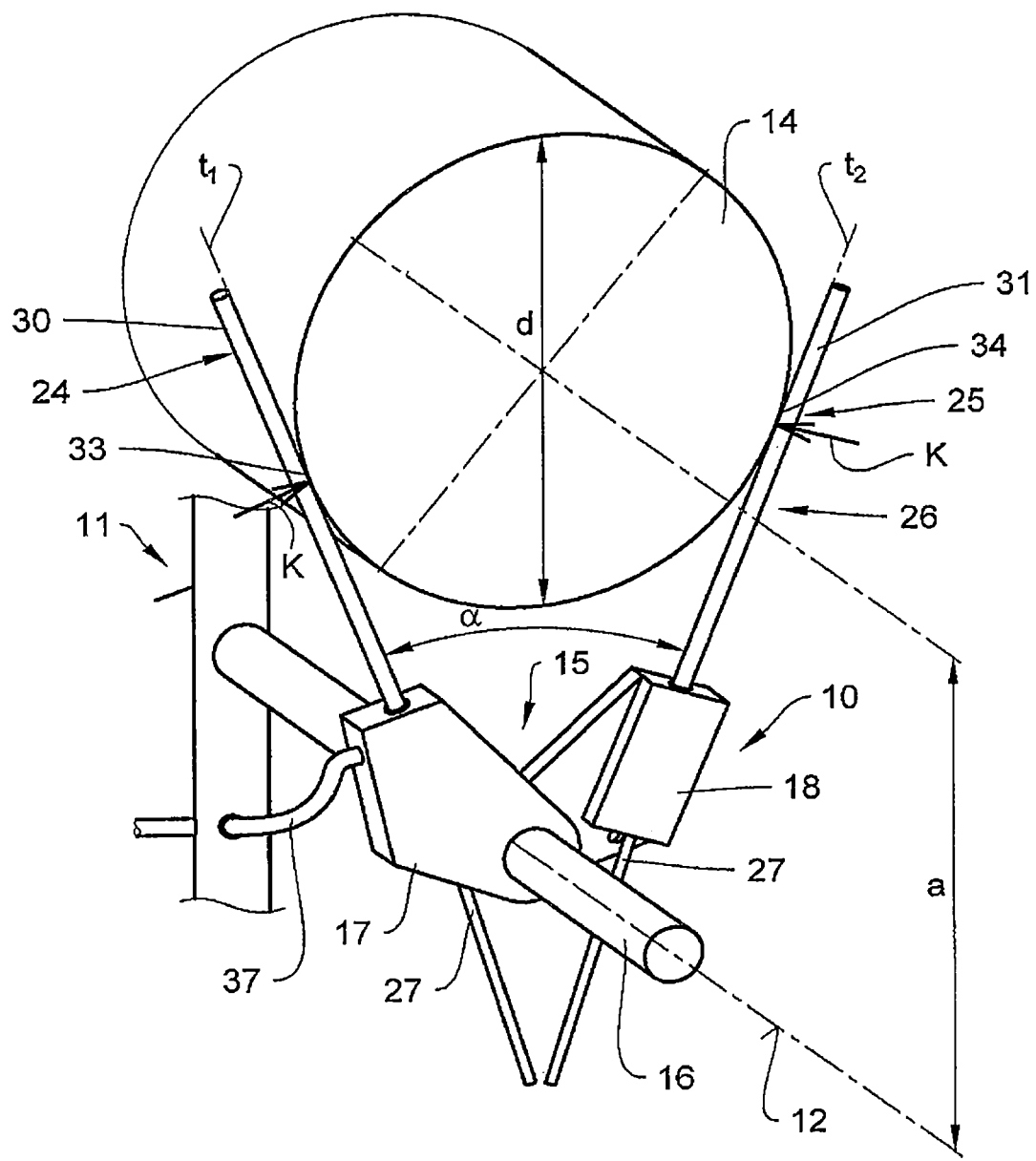
FIG. 1: shows an isometric illustration of a discharging device arranged on a shaft and comprising a holder and a conductor arrangement arranged on the holder.

FIG. 1 shows a discharging device 10 which is arranged in a machine housing 11 and serves to discharge a static charge of a shaft 14 housed in the machine housing 11, the shaft being a gear shaft or a motor shaft, for example.

The discharging device has a holder 15 which has two holder legs 17 and 18 mounted on a bolt 16.

Figure 2:
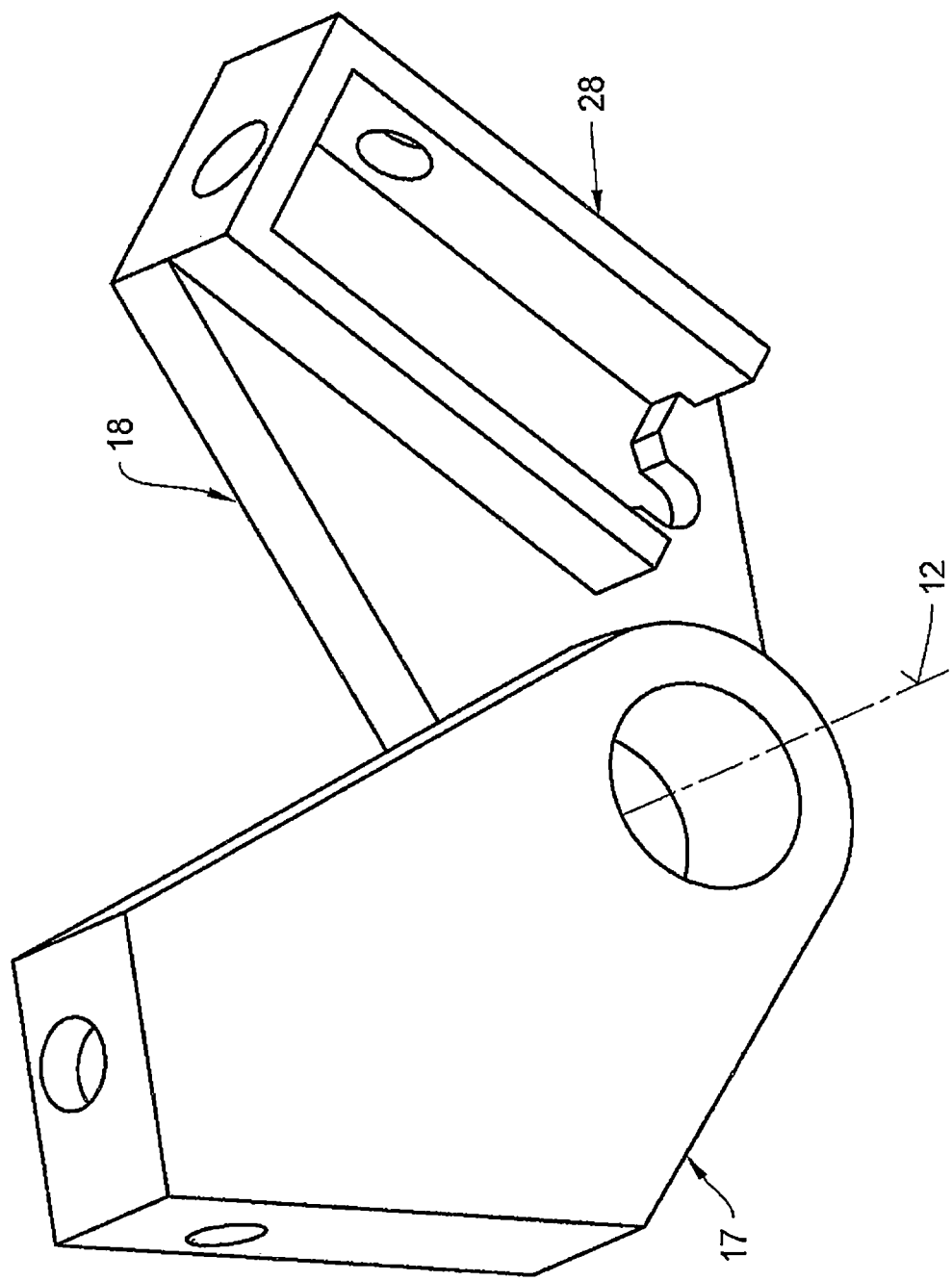
FIG. 2: shows the holder illustrated in FIG. 1 with two holder legs pivotable relative to each other about a pivot axis.
Figure 3:
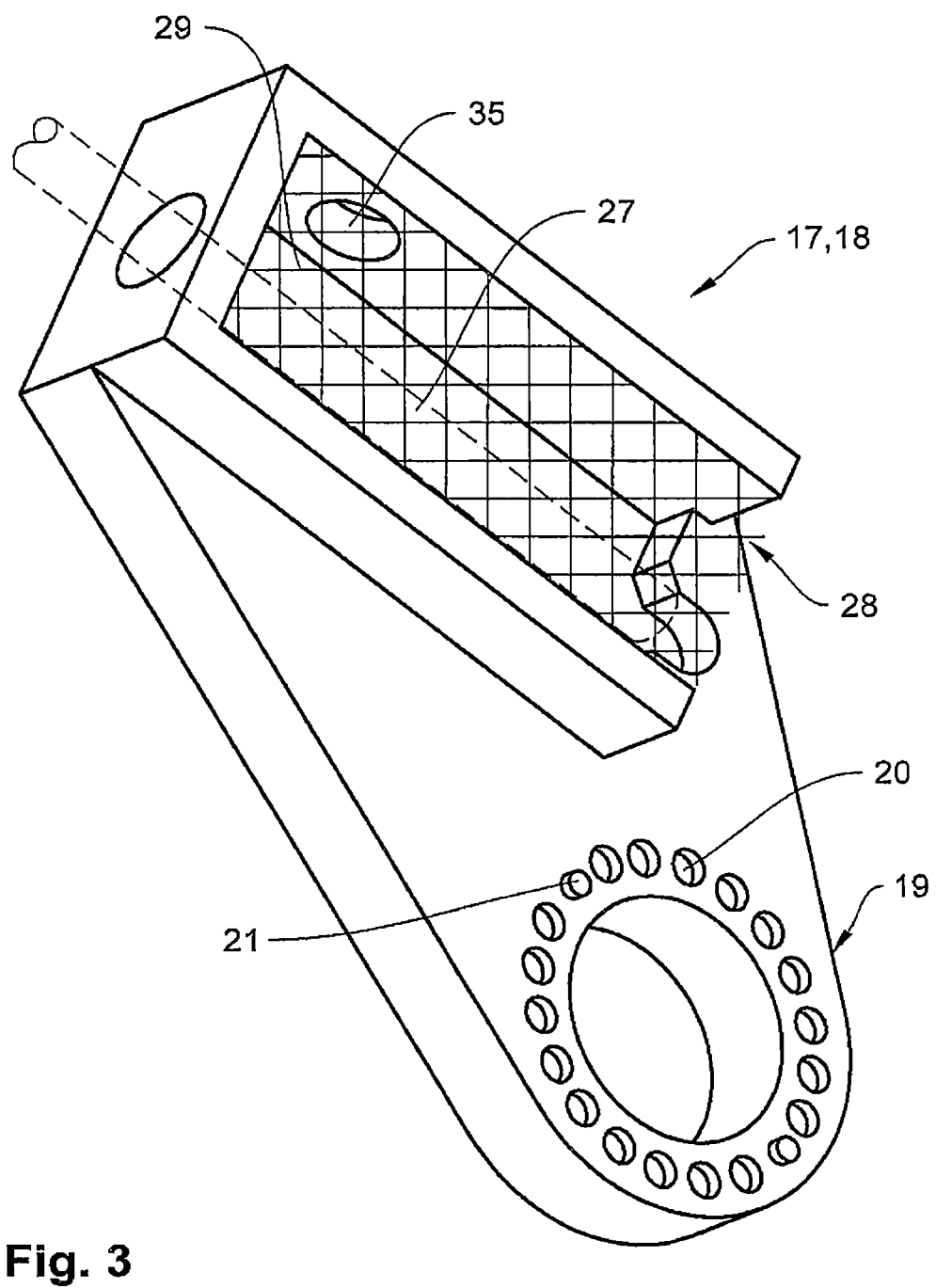
FIG. 3: shows an individual holder leg of the holder illustrated in FIG. 2.

The holder legs 17, 18 forming the holder 15, which is illustrated in FIG. 2 as well, are of identical design in the case at hand, and, as illustrated in FIG. 3, each holder leg 17, 18 has an eyelet 19 with which the holder legs 17, 18 are arranged on the bolt 16 so as to be pivotable about a pivot axis 12. Each holder leg 17, 18 has locking elements arranged equidistantly at the circumference of the eyelet 19 and formed as locking openings 20 and as locking protrusions 21. When the holder legs 17, 18 are arranged on the bolt 16 in such a manner that contact surfaces 22 of the holder legs 17, 18 that are provided with the locking openings 20 and to with the locking protrusions 21 are located opposite each other, the pivoted position of the holder legs 17, 18, which is illustrated exemplarily in FIG. 1, can be fixed at a holder angle α formed between the holder legs 17, 18 by means of the engagement of the locking protrusions 21 of one holder leg 17 into the locking openings 22 of the other holder leg 18. The locking protrusions 21 of holder leg 17 form a locking means 23 together with the locking openings 22 of holder leg 18.

As FIG. 1 shows, a conductor 24, 25 of a conductor arrangement 26 is arranged on each of the holder legs 17, 18 in such a manner that a terminal section 27 of each conductor 24, 25 is accommodated in a mold cavity 28 formed on each of the holder legs 17, 18 as illustrated in FIG. 3. For a mechanically secure connection with the holder leg 17, 18 and for forming an electrical contact with the holder leg 17, 18, the terminal section 27 in the case at hand is embedded into an electrically conductive filling material 29 filled into the mold cavity 28. Alternatively, it is also possible to produce an electrically conductive fixed connection between the terminal section 27 and the holder leg 17, 18 by connecting the terminal section 27 to the holder leg 17, 18 in a force-fitting manner via a clamping screw (not illustrated) or the like which protrudes into the mold cavity 28 through a passage opening 35.

As FIG. 1 shows, shaft contact sections 30, 31 of the conductors 24, 25, which are realized as contact fiber strands in the case at hand, form a V-shaped conductor arrangement 13 corresponding to the holder angle α formed by the relative pivoted position of the holder legs 17, 18 and are in tangential contact with a shaft circumference 32 in circumference contact areas 33, 34, the shaft contact sections 30, 31 being in elastically resilient contact with the shaft circumference 32 in the circumferential contact areas 33, 34 with a contact force K owing to the bending-elastic design of the conductors 17, 18. This is particularly evident from the illustration of touching tangents t1 and t2, which are depicted in the circumferential contact areas 33, 34 in FIG. 1.

It becomes clear from the illustration in FIG. 1 that the discharging device basically offers two options to influence the contact force K, one being an adjustment of the holder angle α and the other being the adjustment of the holder distance a, the holder distance a being the distance between the pivot axis 12 and the shaft longitudinal axis 36 of the shaft 14. Furthermore, the holder angle α and the holder distance a represent the possible parameters that allow adapting the discharging device 10 to different shaft diameters d.

In the embodiment example illustrated in FIG. 1, a charge is electrically discharged by means of a grounding conductor 37 connected to the holder leg 17, provided with an insulating sheath and guided through the machine housing 11.

The invention claimed is:

1. A discharging device for discharging electrostatic charges from a shaft, said discharging device comprising:
   a conductor arrangement having at least two bending-elastic conductors;
   terminal sections for connecting the conductors to a grounding, each terminal section having a shaft contact section, the shaft contact sections forming a contact arrangement for making contact with two circumferential contact areas of a shaft circumference, the contact areas being arranged opposite each other in a shaft contact plane W, in such a manner that the shaft contact sections are arranged tangentially to the shaft circumference when they are in contact with the shaft circumference; and
   a holder accommodating said terminal sections and on which said conductor arrangement is arranged, said holder being made of a carbon-fiber arrangement and running transverse to a shaft longitudinal axis, the holder having two holder legs arranged on a common pivot axis, each holder leg accommodating one of said terminal sections and the holder legs being pivotable against each other in order for a holder angle α formed between the holder legs to be adjusted and the holder legs being lockable in a defined pivoted position.

2. The discharging device according to claim 1, in which the conductors of the conductor arrangement are two mutually independent conductor strands which are connected to each other in an electrically conductive manner via the terminal sections.

3. The discharging device according to claim 1,
   in which the terminal sections are connected to each other in an electrically conductive manner via the grounding conductor.

4. The discharging device according to claim 1,
   in which the terminal sections are connected to each other in an electrically conductive manner via the holder legs.

5. The discharging device according to claim 4,
   in which the holder legs are made of an electrically conductive material.

6. The discharging device according to claim 5,
   in which the holder legs are made of a carbon material.

7. The discharging device according to claim 1, in which the pivot axis is formed by a bolt connecting the holder legs and being realized independently from the holder legs.

8. The discharging device according to claim 7, in which the holder legs are made of an electrically conductive material and the bolt is made of an electrically nonconductive material.

9. The discharging device according to claim 1, in which for accommodating the terminal sections of the conductors, the holder legs have a mold cavity for receiving a filling material embedding the terminal sections.

10. The discharging device according to claim 1, in which a lock formed between the holder legs locks the holder legs relative to each other.

11. The discharging device according to claim 1, in which the carbon-fiber arrangement of the conductors has a fiber network that is provided with a coating made of pyrolytically deposited carbon.

12. The discharging device according to claim 11, in which the fiber network is realized as an envelope of a unidirectional fiber strand extending in the longitudinal direction of the conductors.

13. The discharging device according to claim 11 in which the fiber network is provided with a resin matrix.

14. The discharging device according to claim 5, in which the holder legs are made of graphite.

* * * * *

UNITED STATES PATENT AND TRADEMARK OFFICE
CERTIFICATE OF CORRECTION

PATENT NO. : 10,660,188 B2
APPLICATION NO. : 15/521826
DATED : May 19, 2020
INVENTOR(S) : Gerhard Denner Page 1 of 1

It is certified that error appears in the above-identified patent and that said Letters Patent is hereby corrected as shown below:

In the Specification

Column 4, Line 17, "and to with the" should be --and with the--.

Signed and Sealed this
Fourteenth Day of July, 2020

Andrei Iancu
*Director of the United States Patent and Trademark Office*